United States Patent [19]

Ryan et al.

[11] Patent Number: 5,285,795
[45] Date of Patent: Feb. 15, 1994

[54] PERCUTANEOUS DISCECTOMY SYSTEM HAVING A BENDABLE DISCECTOMY PROBE AND A STEERABLE CANNULA

[75] Inventors: Timothy J. Ryan, San Francisco; Charles J. Winslow, Walnut Creek, both of Calif.

[73] Assignee: Surgical Dynamics, Inc., Concord, Calif.

[21] Appl. No.: 758,806

[22] Filed: Sep. 12, 1991

[51] Int. Cl.$^5$ .................. A61B 10/00; A61B 1/00; A61B 17/20

[52] U.S. Cl. .................. 128/750; 128/749; 128/751; 128/4; 128/6; 606/15; 606/16; 606/170; 606/171; 604/22

[58] Field of Search .................. 128/4-6, 128/749-754, 783, 786; 604/95, 22; 606/1-2, 9-10, 13-17, 170-171, 176-177, 182

[56] References Cited

U.S. PATENT DOCUMENTS

| | | |
|---|---|---|
| Re. 33,258 | 7/1990 | Onik et al. . |
| 387,454 | 8/1888 | Siegenthaler . |
| 1,906,678 | 6/1931 | Wappler . |
| 2,118,631 | 5/1938 | Wappler . |
| 2,828,744 | 4/1958 | Hirsch et al. . |
| 3,401,684 | 9/1968 | Dremann . |
| 3,521,620 | 7/1970 | Cook . |
| 3,537,451 | 11/1970 | Beck Murray . |
| 3,547,103 | 12/1970 | Cook . |
| 3,592,192 | 7/1971 | Harautuneian . |
| 3,614,953 | 10/1971 | Moss . |
| 3,732,853 | 5/1973 | Banko . |
| 3,815,604 | 6/1974 | O'Malley . |
| 3,844,272 | 10/1974 | Banko .................. 606/170 |
| 3,884,238 | 5/1975 | O'Malley . |
| 3,935,857 | 2/1976 | Co . |
| 3,937,222 | 2/1976 | Banko . |
| 3,948,273 | 4/1976 | Sanders . |
| 3,949,471 | 4/1976 | Cawley . |
| 4,210,146 | 7/1980 | Banko . |
| 4,273,128 | 6/1981 | Lary . |
| 4,368,730 | 1/1983 | Sharrock . |
| 4,493,694 | 1/1985 | Wuchinich . |
| 4,513,745 | 4/1985 | Amoils . |
| 4,517,977 | 5/1985 | Frost . |
| 4,573,448 | 3/1986 | Kambin . |
| 4,636,346 | 1/1987 | Gold et al. . |
| 4,650,472 | 3/1987 | Bates . |
| 4,679,459 | 7/1987 | Onik et al. . |
| 4,702,260 | 10/1987 | Wang .................. 128/751 |
| 4,732,163 | 3/1988 | Bonello . |
| 4,756,708 | 7/1988 | Martin . |
| 4,773,395 | 9/1988 | Suzuki et al. .................. 128/4 |
| 4,863,430 | 9/1989 | Klyce et al. . |
| 4,911,148 | 3/1990 | Sosnowski et al. .................. 128/6 |
| 4,955,882 | 9/1990 | Hakky .................. 606/14 |
| 5,041,108 | 8/1991 | Fox et al. .................. 606/15 |

FOREIGN PATENT DOCUMENTS

| | | |
|---|---|---|
| 0086048 | 8/1983 | European Pat. Off. . |
| 0110560 | 6/1984 | European Pat. Off. . |
| 0127261 | 12/1984 | European Pat. Off. . |
| 8101363 | 5/1981 | PCT Int'l Appl. . |
| 2007093 | 5/1979 | United Kingdom . |
| 2018601 | 11/1979 | United Kingdom . |

OTHER PUBLICATIONS

Brochure-Storz Microvit Vitrectomy System-1988.
Brochure-Storz Irrigation Aspiration System-1983.

*Primary Examiner*—Randall L. Green
*Assistant Examiner*—A. Zuttarelli
*Attorney, Agent, or Firm*—Fliesler, Dubb, Meyer & Lovejoy

[57] ABSTRACT

A percutaneous discectomy system 20 having a bendable discectomy probe 22 and steerable cannula 24 allows for a wide range of positions relative to the discectomy tissue to be severed. The bendable discectomy probe 22 includes a bendable section 78, 86 which can allow the probe 22 to be bent more than 90° and still maintain the function required in order to sever and remove tissue. The steerable cannula 24 has a similar bendable section 102 which can appropriately position the end 50 of the discectomy probe 22 in order to address tissue to be removed.

27 Claims, 12 Drawing Sheets

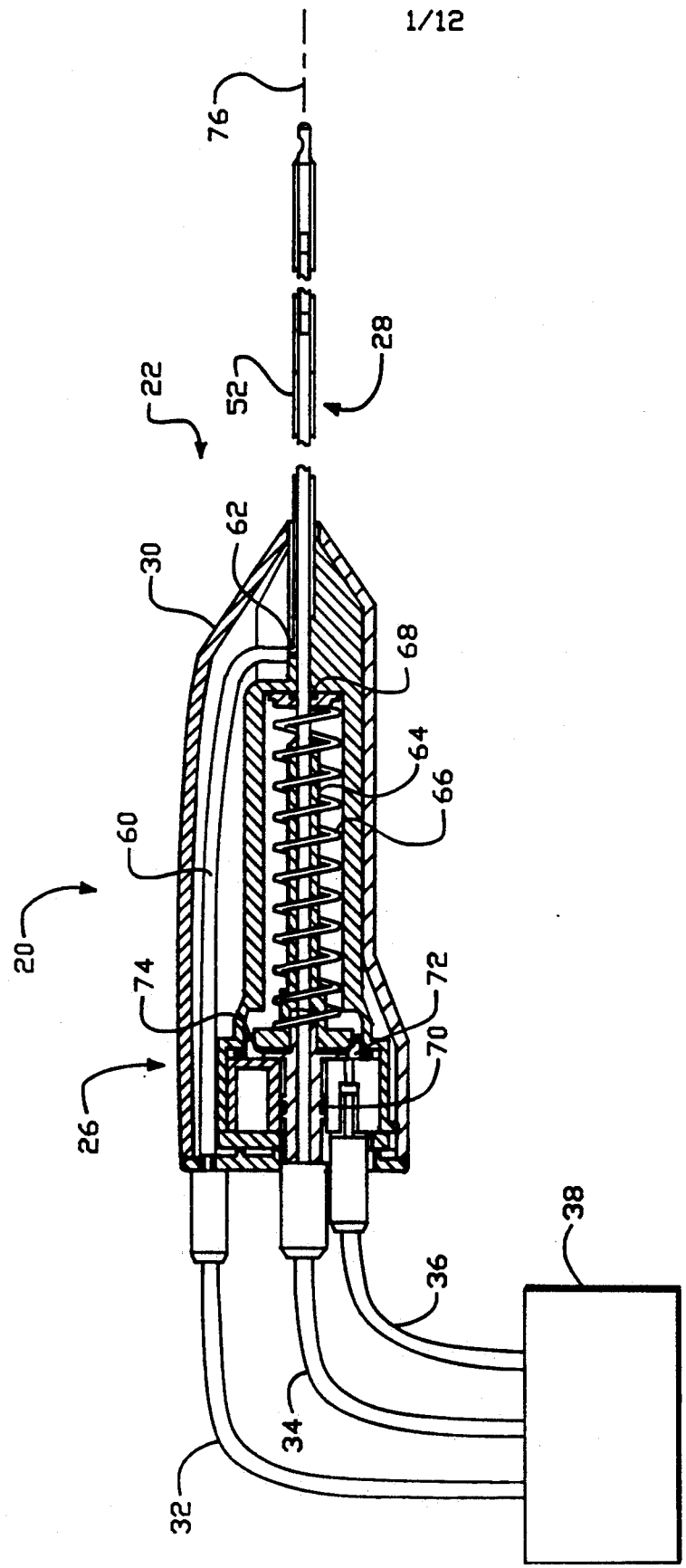
FIG.—1

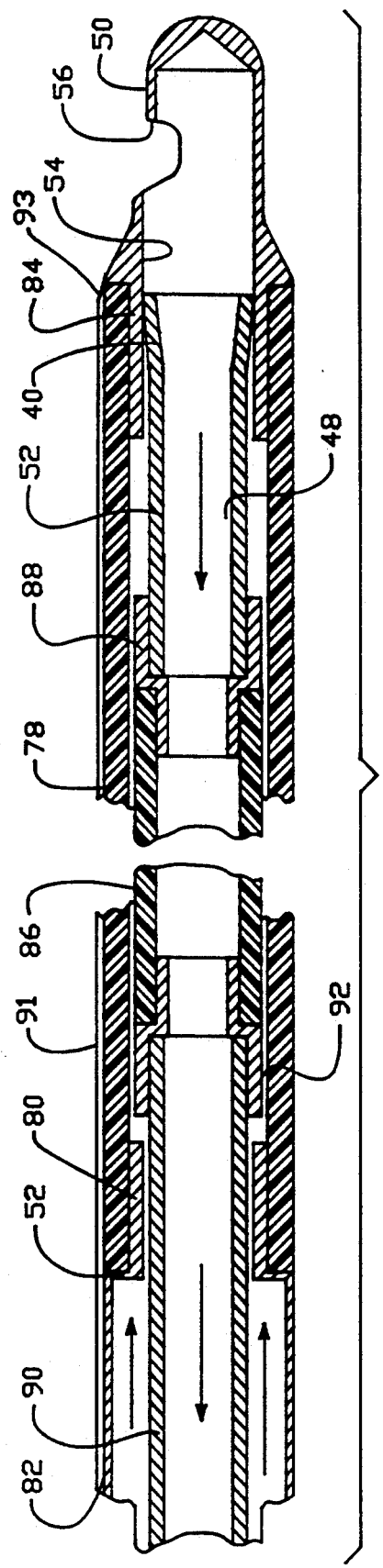
FIG.—2
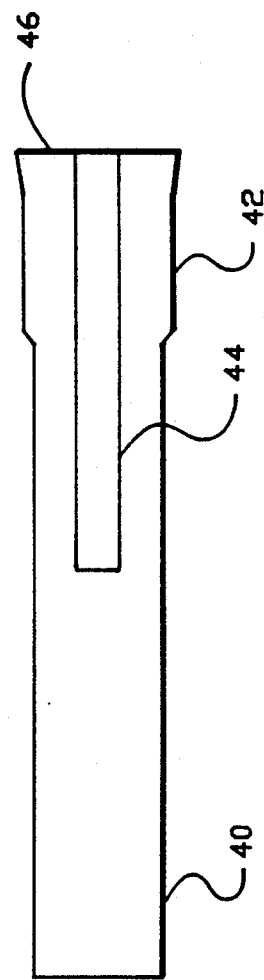
FIG.—3

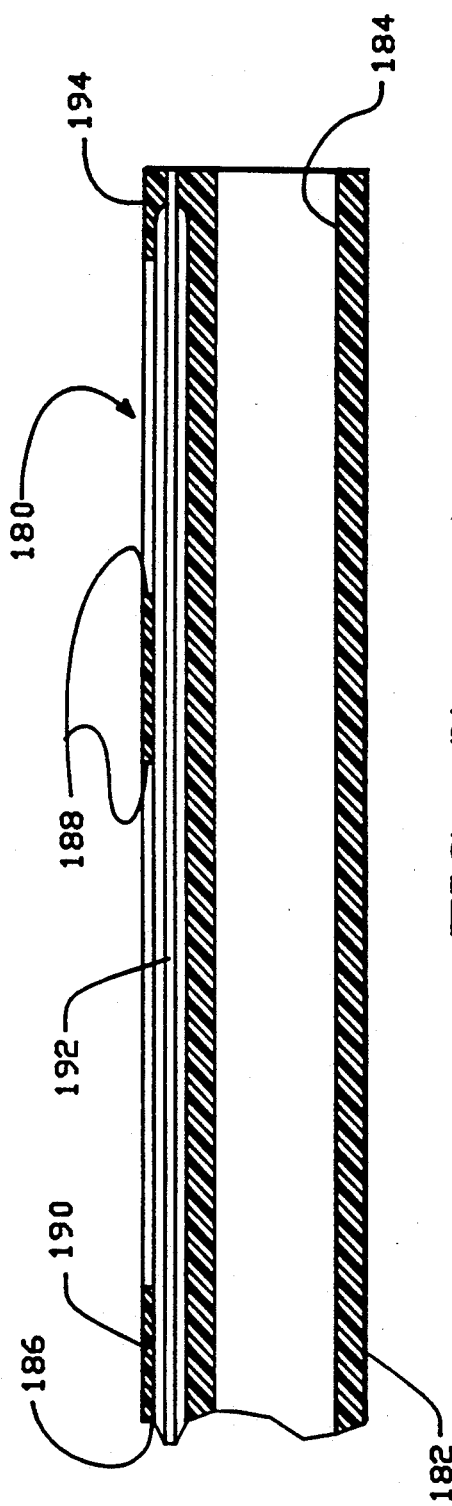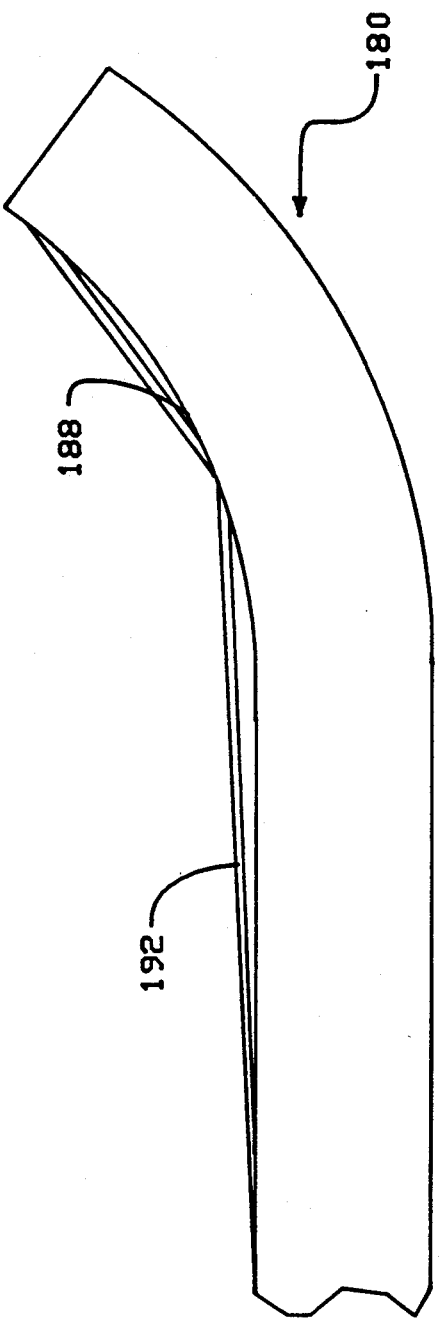
FIG.—7
FIG.—8

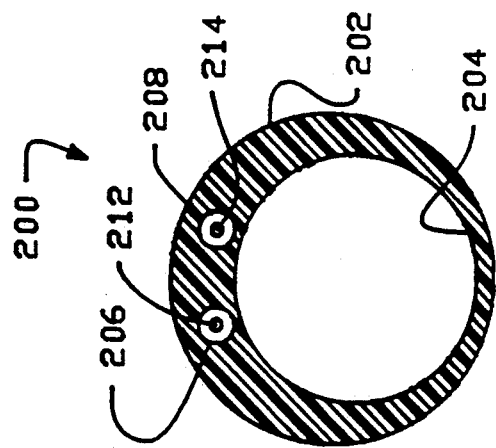
FIG.—10
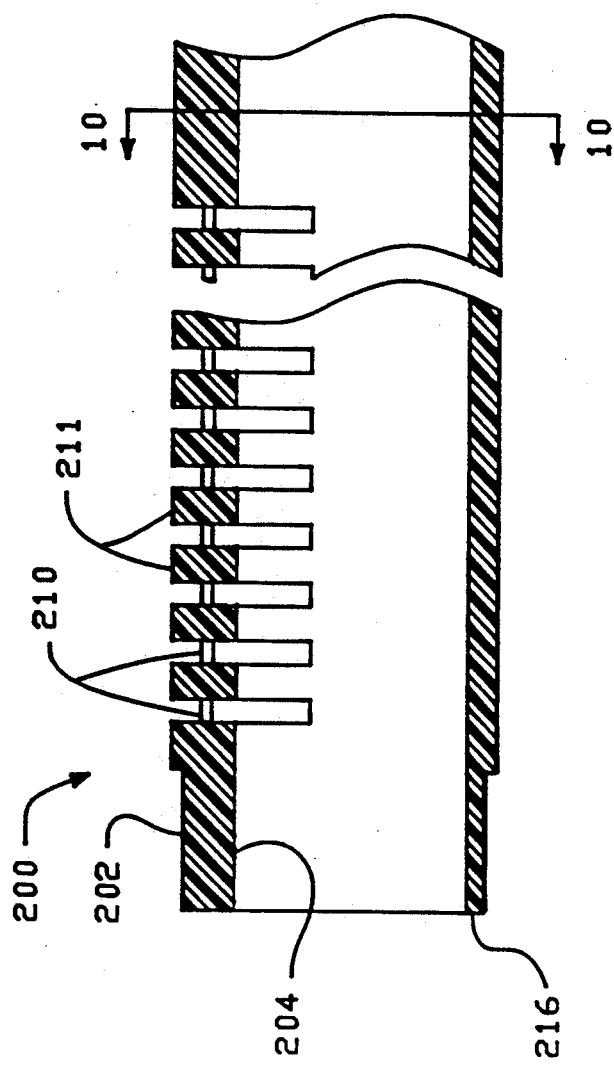
FIG.—9

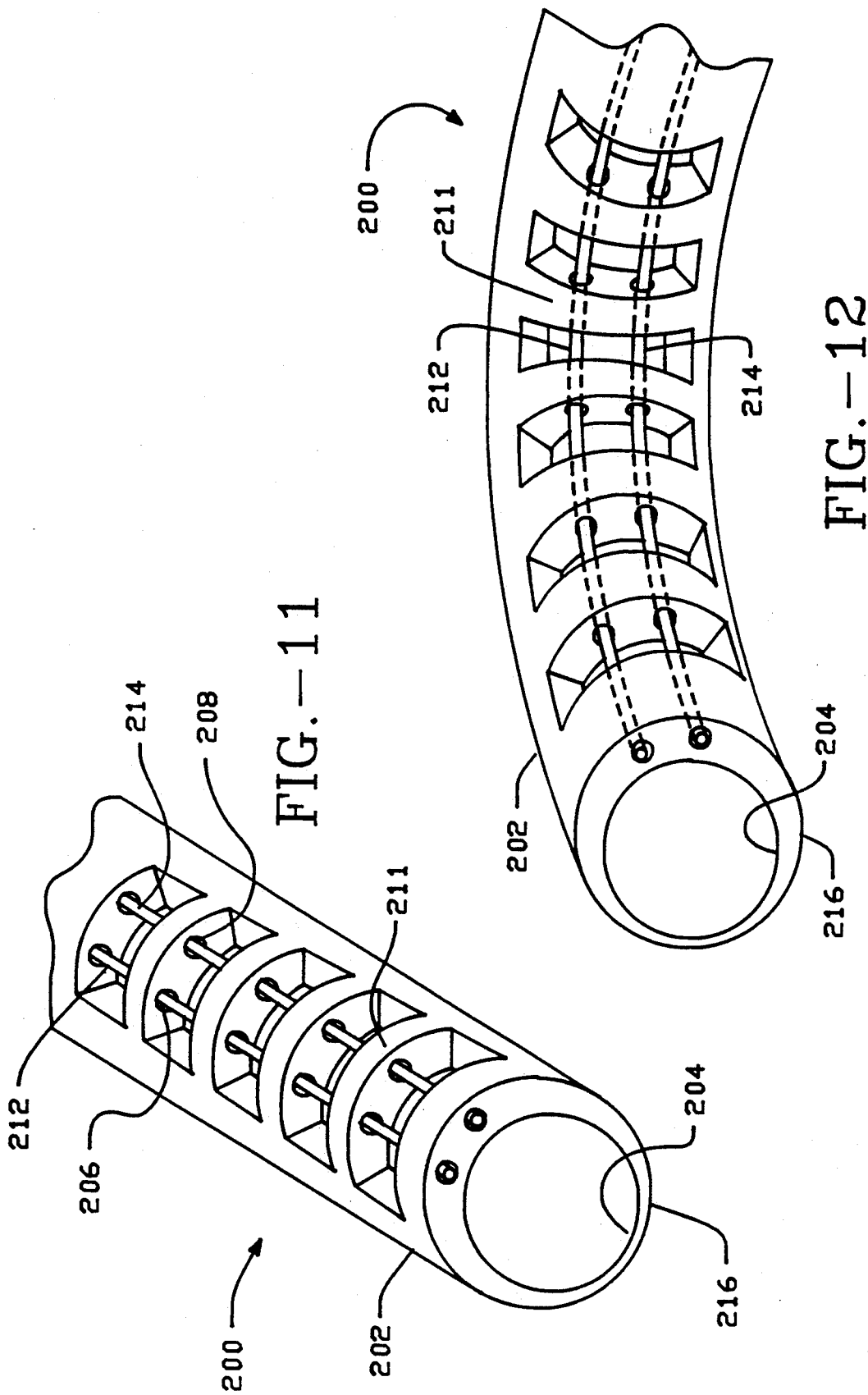

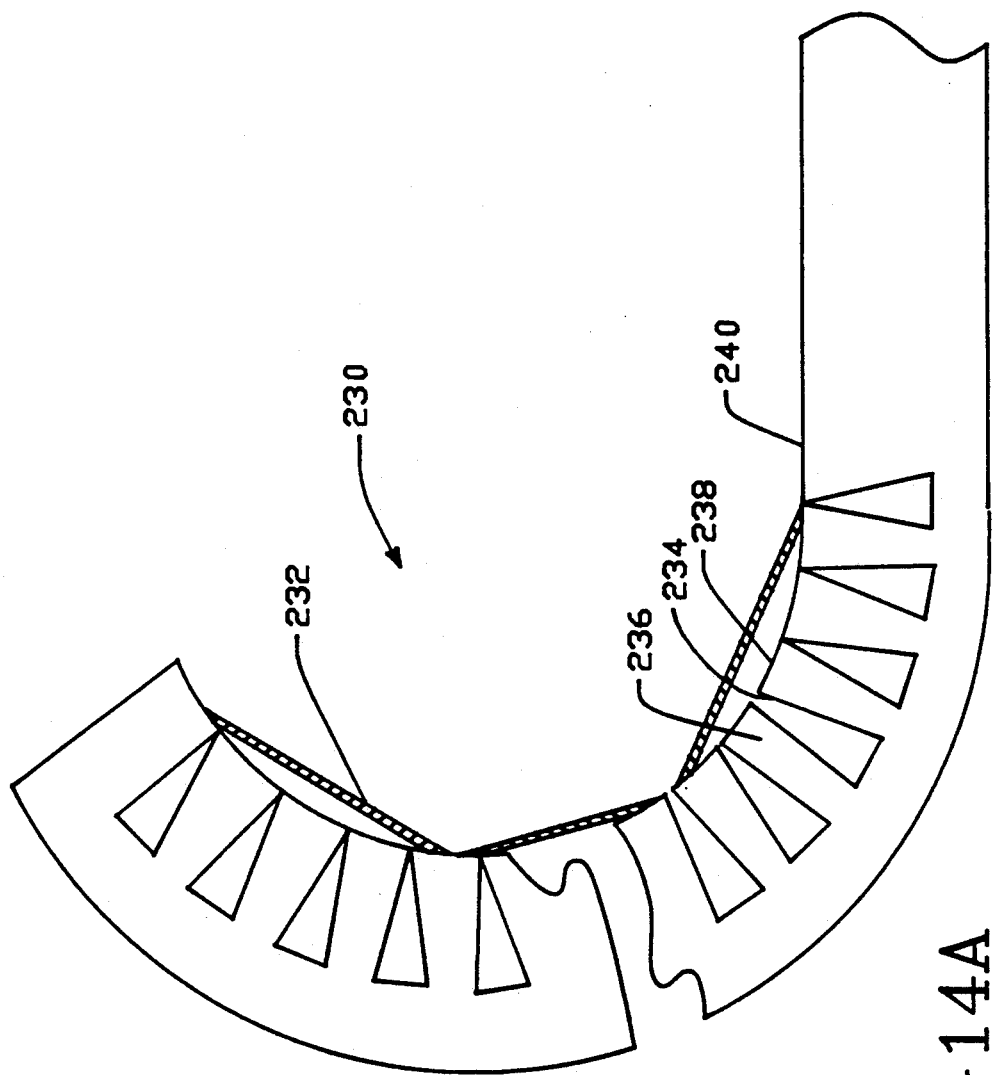
FIG.—14A

PERCUTANEOUS DISCECTOMY SYSTEM HAVING A BENDABLE DISCECTOMY PROBE AND A STEERABLE CANNULA

RELATED CASE

The present case is related to U.S. Pat. Application Ser. No. 07/625,832 filed on Dec. 11, 1990 entitled "PERCUTANEOUS SURGICAL SYSTEM WITH ROTARY CUTTING BLADE" and assigned to Surgical Dynamics Inc., the present assignee. This reference is incorporated herein by reference. To the extent allowable under the law, the assignee claims priority from the filing date of the above-identified application with respect to this present application.

TECHNICAL FIELD

The present invention is related to surgical cutting devices and in particular to a percutaneous discectomy device for removing nucleus pulposus from a herniated spinal disc.

BACKGROUND ART

Presently available from the assignee, Surgical Dynamics, Inc., is a highly successful Nucleotome ® discectomy system manufactured in accordance with the teachings of U.S. Pat. No. Re. 33,258 issued on Jul. 10, 1990 and entitled "IRRIGATING, CUTTING AND ASPIRATING SYSTEM FOR PERCUTANEOUS SURGERY" and U.S. Pat. No. 4,863,430 issued on Sept. 5, 1989 and entitled "INTRODUCTION SET WITH FLEXIBLE TROCAR WITH CURVED CANNULA" both assigned to Surgical Dynamics, Inc., which patents are incorporated herein by references. These patents teach a percutaneous discectomy probe which has been used to greatly minimize the risks of the surgery required for the removal of herniated disc material. Additionally these devices have significantly reduced the time and degree of difficulty required in performing such procedures as well as the recovery time experienced by the patient. Essentially these patents describe a reciprocating or guillotine type cutter which is positioned at the end of an elongated stainless steel probe. With the aid of a straight or curved cannula inserted into the patient, the elongated probe can be used to address a herniated disc located between the various adjacent vertebrae. The curved cannula can be positioned to address the difficult to reach discs located in the lumbar region. Once the curved cannula is positioned using a trocar and fluoroscopic imaging, the curved cannula can to some extent cause the elongate probe to flex as the probe is inserted through the curved cannula in order to address and removed herniated disc tissue.

While these devices have been highly successful, the need has arisen to make the Probe more maneuverable in order to remove more of the herniated disc material without having to reintroduce and reposition the curved cannula and probe relative to the herniated disc. A greater maneuverability would reduce the time required for the operation and the trauma to the adjacent bodily tissues.

SUMMARY OF THE INVENTION

Accordingly, the present invention is directed to satisfying the need of providing a discectomy probe which is bendable and steerable so that an increased amount of herniated disc material can be removed through one entry point in the patient's body.

In accordance with the present invention, a surgical instrument comprises a probe body and an elongated probe needle, with a longitudinal axis, extending from the probe body. The probe needle includes a device adapted for removing tissue and a highly and repeatedly bendable section which is located adjacent to the tissue removing device in order to allow for selective positioning of the tissue removing device through a wide range of positions relative to the longitudinal axis. The probe further includes a substantially rigid section which is located between the bendable section and the probe body.

In a further aspect of the invention, the repeatedly bendable section allows the tissue removing means to be repeatedly positioned to a location at least about 90° from the longitudinal axis.

In a further aspect of the invention, the probe needle provides for the passage of irrigation fluid through the bendable section so that it can be delivered to the tissue removing device as well as the aspiration of fluid from the tissue removing device through the bendable section to a collection device.

Yet in another aspect of the invention, the fluid irrigation is provided through a first passage and aspiration is provided through a second passage which is located relative to the first passage. The first passage includes a first elastic portion and the second passage include a second elastic portion with the first and second elastic portions comprising the bendable section of the probe.

In another aspect of the invention, the tissue removing means includes a reciprocating cutting blade, which reciprocates past a port in the needle in order to sever herniated disc tissue.

In yet another aspect of the invention, a tissue removing means includes a means for delivering light capable of removing the tissue. Such light can be delivered from a source such as a laser. In this embodiment, the requirement for providing irrigating fluid is eliminated. However, a provision is made for aspiration of fluids from the surgical site.

In yet another aspect of the invention, the invention includes a steerable cannula with an internal passage capable of delivering and steerably positioning the probe needle. The steerable cannula includes a bendable portion and a substantially rigid portion. There is a tether or other appropriate device between the bendable and the rigid portion, and a device for moving the tether and bendable portion relative to the rigid portion so as to position the tissue removing device of the probe needle with the probe needle received in the internal passage of the cannula.

Such an arrangement provides for enhanced positioning capabilities of the tissue removing device of the invention. Once the steerable cannula is positioned through the bodily tissues and relative to the herniated disc with the aid of a trocar and fluoroscopic imaging, the cannula itself can be steered and positioned relative to the herniated disc. With such steerability, the cannula provides for the positioning of the end of the cannula through 360°. After the cannula is positioned, the probe can be inserted through the cannula and extended out the end of the cannula varying distances in order to cut tissue along a linear path which extends from the end of the cannula. Once the tissue in this path has been removed, the probe can be drawn back into the cannula and the cannula repositioned by means of the tether lines or other appropriate devices. After the cannula has been repositioned, the probe can again be reextended through the end of the cannula in order to sever tissue along a line which extends from the end of the cannula.

Accordingly, substantially any desired disc location can be addressed within the three degrees of freedom of mobility which are afforded by the present system combining the bendable probe and the steerable cannula.

It is to be understood that other tissues in addition to disc tissue can be removed using embodiments of the invention.

Other inventive aspects can be obtained by a review of specification, the claims and the appended figures.

BRIEF DESCRIPTION OF THE FIGURES

FIG. 1 depicts a cross-section view of a percutaneous discectomy probe of the invention.

FIG. 2 depicts a portion of the embodiment of FIG. 1 and in particular an enlarged depiction of the bendable section.

FIG. 3 depicts a side view of the reciprocating cutting blade or guillotine cutting blade of the invention of FIG. 2.

FIG. 7 depicts a cross-sectional view of an alternative embodiment of the steerable cannula with apertures provided through the cannula wall at spaced intervals in order to allow the tether to emerge.

FIG. 8 depicts a side view of the embodiment of FIG. 7 with the cannula proved in a curved position due to the action of the tether.

FIG. 9 depicts an alternative embodiment of the curved cannula with spaced apart segments in order to increase the steerability of the cannula.

FIG. 10 depicts a cross-sectional view of FIG. 9 as shown at line 10—10.

FIG. 11 depicts a perspective view of the steerable cannula of FIG. 9.

FIG. 12 depicts a perspective view of the embodiment of the steerable cannula of FIG. 9 provided in a bent position.

FIGS. 14A and 14B depicts an alternative embodiment of the steerable cannula including some of the advantages of the embodiment of FIG. 7 and of the FIG. 9.

DETAILED DESCRIPTION OF THE PREFERRED EMBODIMENT

Figures 4, 5:
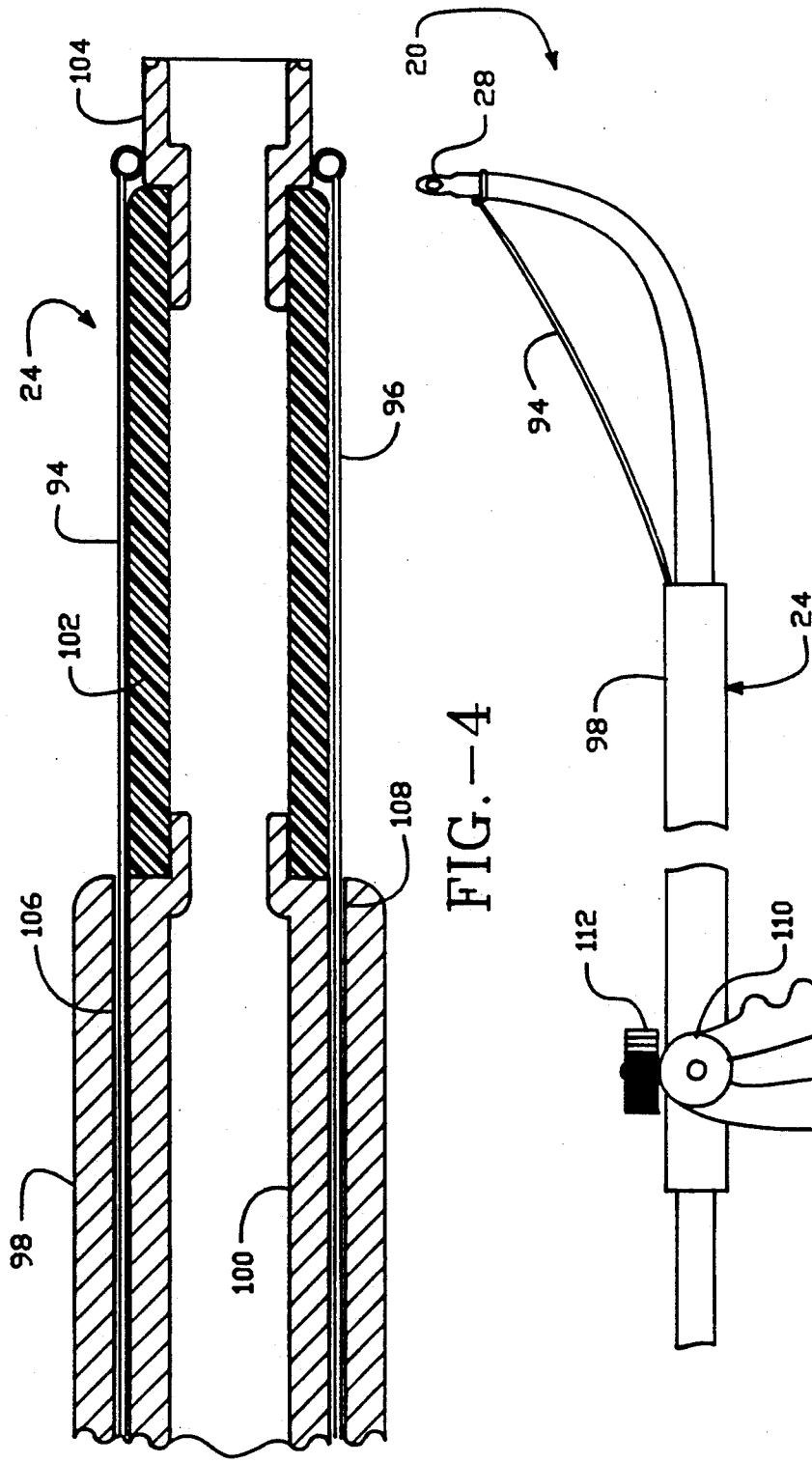
FIG. 4 depicts a partial and sectioned view of a steerable cannula of the invention.
FIG. 5 depicts a view of the entire steerable cannula of an embodiment of the invention with the bendable probe of FIG. 1 positioned through the steerable cannula with the tether of the steerable cannula retracted in order to reposition the end of the probe relative to the longitudinal axis of the probe needle.

With reference to the figures and in particular FIG. 1, the preferred embodiment of the percutaneous discectomy system 20 with a bendable discectomy probe 22 is depicted. The system 20 further includes a steerable cannula 24 which is shown in FIGS. 4 and 5.

As can be seen in FIG. 1, the bendable probe 22 includes a probs body 26 with a probe needle 28 extending therefrom. Probe needle 28 is, in a preferred embodiment, elongate and has a diameter preferably of between 2 and 3 millimeters.

The probe body 26 is designed to function in a manner which is similar to that defined in the above-mentioned issued patents which have assigned to Surgical Dynamics, Inc. Basically, the probe body 26 includes an outer housing 30 and extending from the back end thereof irrigation conduit 32, aspiration conduit 34, and actuation or pressure pulse conduit 36. These conduits 32, 34, and 36 are provided to a controller 38 which operates much in the manner of the controller described in above U.S. Pat. No. Re 33,258.

As can be seen in FIGS. 1 and 2, the bendable probe 22 and in particular the probe needle 28 includes an elongate tubular cutting member 40 which has at its end a flared guillotine-type cutter 42 and a slot 44 which open to the flared end 46 of the guillotine cutter 42 in order to allow irrigation fluid, as will be described hereinbelow, to be provided to the end 50 of the probe needle 28. The tubular cutting member 40 defines a central bore 48 which communicates with the slot 44. Positioned about the elongate tubular cutting member 40 is an elongated outer probe needle housing 52. The guillotine cutter 42 can reciprocate back and forth within the probe needle housing 52 with the flared end 46 provided in contact with the inner cylindrical wall 54 of the probe needle housing 52. The guillotine cutter 42 reciprocates past the port 56 provided through the probe needle housing 52 in order to sever tissue as taught in U.S. Pat. No. Re 33,258. The remainder of the elongate tubular cutting member 40 is spaced from the inner cylindrical wall 54 in order to define an annular passage 58. Through this annular passage 58, irrigation fluid flows so that it can be directed through slot 44 to the port 56 in order to aid in the removal of tissue severed by the guillotine cutter 42. Severed tissue and irrigation fluid is then aspirated through the central bore 48 of the elongate tubular cutting member 40.

The probe body 26 includes a conduit 60 which can communicate irrigation fluid from the irrigation conduit 32 through a port 62 provided in the probe needle housing 52 and to the annular passage 58 so that it can be delivered through the slot 44 to the port 56 at the end 50 of the probe needle 28.

The probe body 26 further includes a conduit 64 which provides communication between the aspiration conduit 34 and the central bore 48 of the tubular cutting member 40. Conduit 64 is slidably mounted in the probe body 26 and is urged in a rearwardly direction by the spring 66. As it is known in the art, O-rings 68 and 70 are provided for preventing leaks between the cutting member 40 and the housing 30 in the first instance, and the conduit 64 and the housing 30 in the second instance. A pressure pulse is provided over conduit 36 and through the probe body 26 to a expandable chamber 72 which is defined by a flexible diaphragm 74. A positive pressure pulse causes the expandable chamber 72 to expand in a forwardly direction. The flexible diaphragm 74 extends forwardly in order to urge the conduit 64 and the elongate tubular cutting member 40 forwardly so that the guillotine cutter 42 and in particular, the end 46 thereof is urged past the port 56 at the end of the probe body 26. As this occurs, tissue is aspirated into the port 56 and severed by the guillotine cutter 42. The then severed tissue and irrigation fluid is aspirated through the central bore 48 of the elongated tubular cutting member 40, through the conduit 64 in the probe body 26 and through the aspiration conduit 34 to the controller 38 and in particular to a collection bottle, in a preferred embodiment.

Observing the probe needle 28 in the enlarged sectioned view of FIG. 2, it is evident that this probe needle 28 is constructed so that it is bendable and preferably bendable in excess of 90° from the longitudinal axis 76 of the needle probe 28.

As can been seen in FIG. 2, the needle housing 52 includes an end 50 which, in a preferred embodiment is comprised of stainless steel. This end 50 is secured by an appropriate glue, such as for example, Loctite® 406 which is a cyanoaorylio ester. Other acceptable glues for medical applications can be used. Secured to shoulders 84 of end 50 is a tubular section 78, which in a preferred embodiment is comprised of an elastic material. The preferred elastic material is sold under the trade name PEBAX® and is a polyether block amide, which is a thermoplastic elastomer. Appropriate braiding, fibers, and coils made out of nylon, graphite, metal and other materials can be incorporated into the bendable section 78 in order to increase the ability of the bendable section 78 to maintain repeated bending of at least 90°, and over, relative to the longitudinal axis 76 of the probe needle 28. Bendable section 78 is in turn glued onto a transition shoulder 80. Transition shoulder 80 is formed on the end of a substantially rigid somewhat flexible portion of 82 of the probe body 26. In a preferred embodiment, the portion 82 is comprised of a medical grade stainless steel. It is to be understood that methods other than gluing can be used to secure various components of this invention together and be within the scope and spirit of the invention.

Further, as can be seen in FIG. 2, the elongate tubular cutting member 40 includes a bendable section 86 which is located adjacent the bendable section 78 of the probe needle housing 52. The guillotine cutter 42, which in a preferred embodiment, is comprised of stainless steel, is glued as is set out above to a transition piece 88 which also in a preferred embodiment, is comprised of stainless steel. The transition piece 88 is then glued to the bendable section 86 which in a preferred embodiment is comprised of materials as defined hereinabove for the other bendable section 78. It is to be understood that in other embodiments, the transition piece 88 can be eliminated with the guillotine cutter 42 having a shoulder such as described hereinabove in order to mate directly to the bendable section 86.

The elongate tubular cutting member 40 further includes a substantially rigid portion 90 which in a preferred embodiment is comprised of stainless steel. This rigid portion 90 is glued to a transition piece 92 which in a preferred embodiment is comprised of stainless steel. The transition piece 92 is then secured to the bendable section 86. Again, as discussed above, the transition piece 92 may be replaced with, for example, a rigid portion 90 which includes a shoulder which can accept the bendable section 86.

As can be seen from the figures, the bendable section 78 is located adjacent to the bendable section 86 and therebetween define a portion of the annular passage 58 which provides irrigation fluid to the guillotine cutter 42. The bendable section 86 defines a portion of the central bore 48 through which irrigation fluid and severed tissues are aspirated from the cutting port 56. The central bore 48 and the annular passage 58, as defined by the bendable sections, bend through more than 90° relative to longitudinal axis 76 of the probe body 26 in order to maintain the irrigating, aspiration and cutting functions of the system 20. The probe body 26 thus can bend as required in order to address the herniated disc.

Alternatively and without the use of the transition pieces, the bendable sections 78, 86 can be counterbored in order to provide for a smooth and uniform outer and inner diameter and surface for the elongate tubular cutting member 40 and for the needle housing 52.

As can be seen in FIG. 2, the probe needle 28 further includes fiber optics 91 which terminates at end 93 adjacent to the port 56. Fiber optics 91 include a light conduit, which in a preferred embodiment, is a visible light conduit for providing a source of illumination to the end 93. Additionally, fiber optics 91 includes an image transmitting conduit which can transmit an image of the surgical site from end 93 back to the control console 38.

Turning to FIGS. 4 and 5, the steerable cannula 24 of the invention is depicted. In this embodiment the steerable cannula includes a plurality of tethers, such as tethers 94 and 96 which are used to steer the cannula. It is to be understood that instead of the two tethers shown, at least four tethers could be used, each tether provided in a spacing of about 90° with respect to the rest of the tethers.

As can be seen in FIGS. 4 and 5, the steerable cannula 24 includes a cannula body 98 which in a preferred embodiment is comprised of a rigid stainless steel tube having a central bore 100. Extending from and glued to cannula body 98 is a bendable section 102 which is comprised of, in a preferred embodiment, the thermoplastic elastomer as described hereinabove. At the end of the bendable section 102 is secured an end 104 which in a preferred embodiment is comprised of stainless steel. The tethers 94, 96 are secured to the end 104 and provided on the outside of the bendable section 102 before entering internal passages 106, 108 defined in the cannula body 98. In a preferred embodiment, the tethers 94, 96 are made of stainless steel wire. As can be seen in FIG. 5, two ratchet type positioning knobs 110, 112 are provided adjacent to a handle 114. The turning of the position knobs 110, 112 cause the tethers to be pulled into the internal passages 106, 108 or extended therefrom in order to bend the bendable section 102 and selectively position the end 104 of the steerable cannula 204 relative to the herniated tissue to be removed. In the embodiment shown in FIG. 5, the positional knob 110 would operate the tether 94 and the positional knob 112 would operate tether 96. Additionally, the entire cannula can be rotated on a longitudinal axis in order to assist in the positioning of the probe needle. So configured, the steerable cannula 24 could position the end 104 thereof and thus the end of the probe needle 28 through a complete 360° arc. With such a high degree of steerability, the steerable cannula 24 can cause the bendable probe 22 to address a wide range of positions in order to effectively remove herniated tissue.

With respect to the ratchet knobs 110, 112 extensions can be added should additional force be required to cause the tethers to deflect the end of the steerable cannula when the steerable cannula is positioned in the body. For example, the handles 114 of the steerable cannula can be incorporated into the ratchet knob 110 in order to provide greater force in turning the ratchet knob 110 with respect to the tether 94. Similar adaptations can be made to the ratchet knob 112.

Other types of steerable cannulas can be employed with the present invention as taught and can be within the spirit and scope of the invention.

It is to be understood that the bendable portions of the bendable probe and the steerable cannula can in other embodiments be comprised of materials other than thermoplastic elastomers. For example, as shown in the above-identified U.S. Pat. Application Ser. No. 07/65,832, flexible tubes comprised of tightly wound stainless wires might also be used to provide the necessary flexibility and bendability.

Alternatively, in order to have a uniform diameter for bore 100, the bendable section 102 can be provided through the cannula body 98 so as to eliminate the shoulder as shown in FIG. 4 where the bendable section 102 mates to the cannula body 98.

Figure 6:
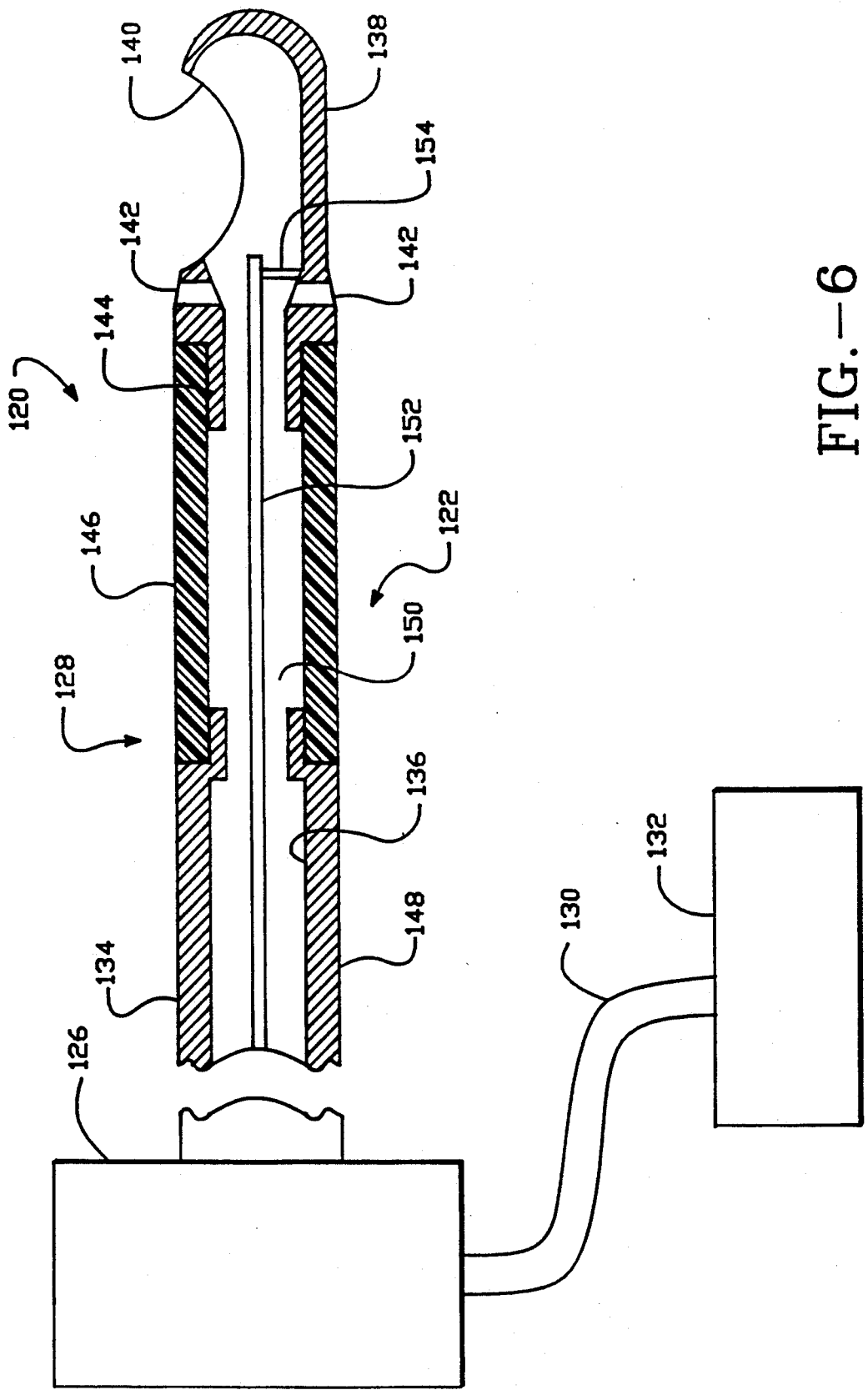
FIG. 6 depicts an alternative embodiment of the bendable probe of the invention using a light source for removing the herniated tissue.

Another embodiment of the present invention is shown in FIG. 6. In this embodiment, a system 120 includes a bendable probe 122 (FIG. 6) and a steerable cannula much as cannula 24 (FIG. 5). Bendable probe 122 includes a probe body 126 from which extends a probe needle 128. Probe body 126 is secured by appropriate conduit 130 to a controller 132. Controller 132 in a Preferred embodiment includes a source of light which is emitted from a laser (such as for example, a KTP/532 laser or a Nd:YAG laser from Laserscope of San Jose, Calif.) and provided through conduit 130 by appropriate fiber optics which in a preferred embodiment is a flexible quartz fiber. In addition an aspiration means is provided in controller 132 in order to aspirate fluids through a passage defined in the conduit 130. As can be seen in FIG. 6, the probe needle 128 includes a probe needle housing 134 which defines an inner cylindrical wall 136. Probe needle housing 134 includes a blunt end 138. Blunt end 138 includes two exhaust passages 142 which can exhaust fluid and in this embodiment, most likely gases developed from the tissue removable process. As can be seen in FIG. 6, the end 138 defines a shoulder 144 which receives a bendable section 146 which can be comprised of any of the materials defined hereinabove such as for example, the thermoplastic elastomers The bendable section 146 is glued to the end 138 in a manner described hereinabove. The bendable section 146 is in turn secured to elongate rigid section 148 which has an appropriate shoulder arrangement for receiving the bendable section 146. Bendable section 146 is glued to the shoulder of the rigid section 148 in a preferred embodiment.

The inner cylindrical wall 136 defines an inner elongate passage 150 which houses fiber optics 152. The fiber optics 152 ends adjacent the port 140 and is secured in position by a mount 154 by methods known in the trade. The fiber optics 152 and the light sources therefor are known in the trade.

In operation, the embodiment of FIG. 6 draws tissue into the port 140. Additionally, tissue is forced into port 140 by adjacent tissue as the probe displaces tissue upon insertion. As this occurs, light from the fiber optics 52 is used to burn the tissue thereby removing it from the herniated disc. This action essentially causes the tissue to become vaporized into a gas which is then removed by aspiration from the areas of the ports 140, 142 through the passage 150 and into a collection mechanism provided in or adjacent to the controller With respect to FIG. 6, the outside of the probe needle housing 134 adjacent to the port 140 is coated in a preferred embodiment with a dry lubricant. Such lubricant is used to greatly reduce the incinerated tissue from becoming stuck to the outside of the probe needle housing 134. A build up of such tissue would make the positioning and placement of the probe needle more difficult. In a preferred embodiment, the dry self-lubricant can include Dycroncrite.

The embodiment of FIG. 6 can be used with the steerable cannula of FIG. 5 in order to position the end 138 and thus the port 140 with the degrees of freedom as previously discussed with respect to the embodiment of the invention as shown in FIGS. 1 and 2.

FIG. 7 depicts an alternative embodiment of the steerable cannula 180 of the invention. In this embodiment, the steerable cannula 180 is comprised of a bendable and flexible section 182 which is comprised of materials as set out hereinabove. In this embodiment, there is a main central bore or lumen 184 which is provided for receiving the probe needle, such as for example, probe needle 28 of FIG. 1. The steerable cannula 180 further includes a side bore or lumen 186 which is substantially smaller than the central bore or lumen 184 and located parallel to and on the side thereof. These bores are provided preferably by molding into the steerable cannula 180. The side bore 186 includes a plurality of elongate ports 188 which are provided in communication with bore 186 and also which communicate with the outer surface 190 of the steerable cannula 180. Provided in the side bore 186 is, in a preferred embodiment, a tether 192 which is anchored in the wall of the steerable cannula 180 at end 194 in accordance with gluing techniques or molding techniques know in the trade.

As can be seen in FIG. 8 with the tether 192 pulled backwardly so that the end 194 begins to bend relative to the longitudinal axis of the cannula, the tether 192 projects from the elongated ports 188 and becomes at some points displaced from the bendable section 182 of the steerable cannula 180.

An alternative embodiment of the steerable cannula is shown in FIGS. 9, 10, 11, 12, and 13 and is identified by the number 200. This cannula as with the other embodiments of this invention is comprised of, in part, a flexible and bendable material which defines a flexible and bendable section 202. Section 202 defines a central bore or lumen 204 and first and second side bores or lumens 206, 208. As can be seen in FIGS. 9, 11 and 12 a plurality of semi-circular slits 210 are provided through the steerable cannula 200. In a preferred embodiment, these slots are 0.04 inches wide and the segments 211 of the flexible and bendable section ZOZ located between slots is, in a preferred embodiment, about the same width. It is to be understood that other widths for the semi-circular slots can be provided and be within the scope and the spirit of the invention.

Disposed in first side bore 206, in a preferred embodiment, is a tether 212 which is similar to the tethers described hereinabove. Providing in the second side bore 208 is a fiber optics cable 214 which can provide both a source of light to the surgical site located adjacent the end 216 of the steerable cannula 200 and also a conduit for returning to the console images from the end 216 of the steerable cannula 200. Fiber optics for providing a source of visible light and for returning an image of an illuminated area as required for the steerable cannula 200 are well known in the trade.

Figure 13:
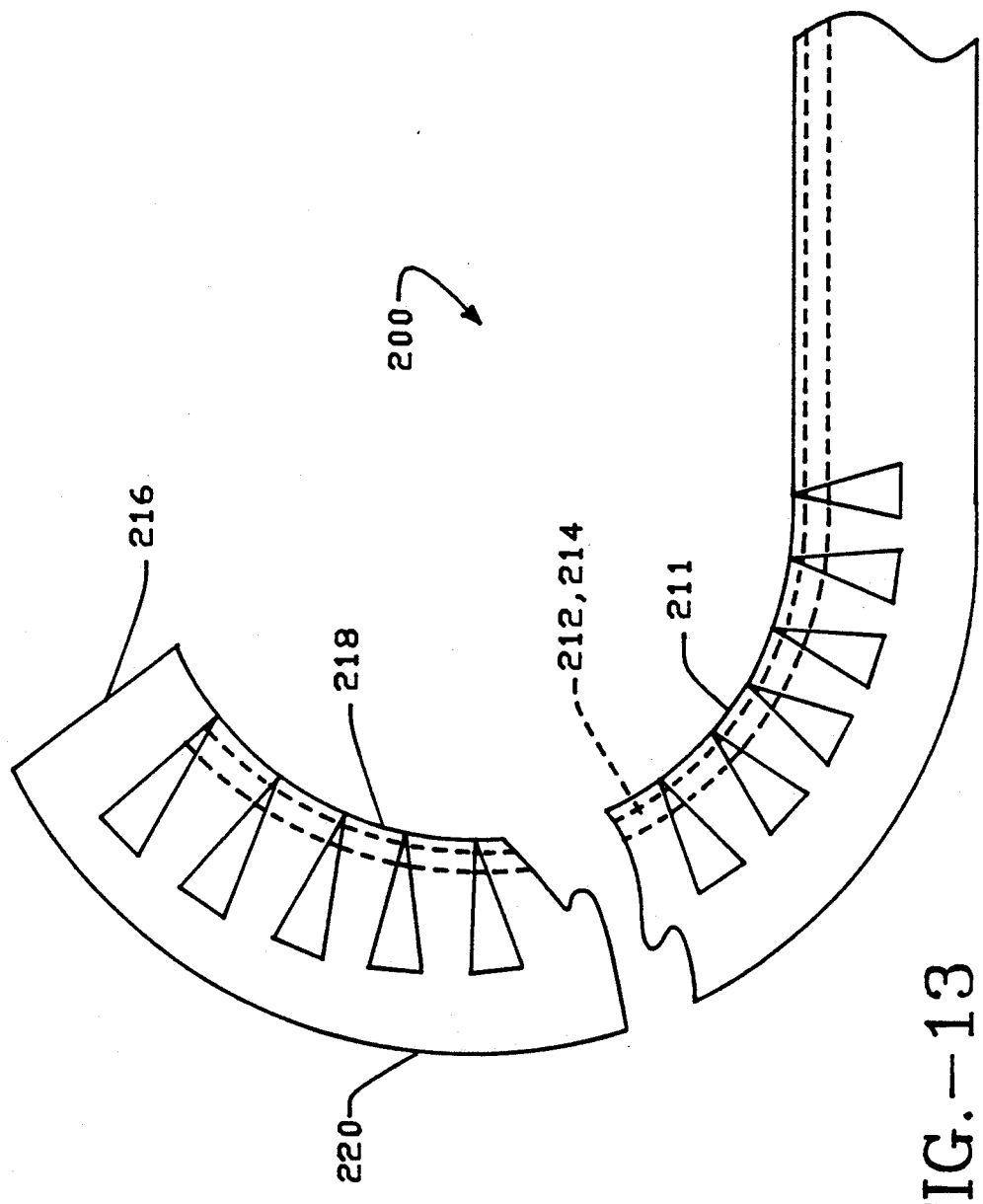
FIG. 13 depicts a side view of the embodiment of the steerable cannula of FIG. 12.

As can be seen in FIGS. 12 and 13, as the tether is drawn back so that end 216 is displaced relative to the longitudinal axis of the steerable cannula 200, the semi-circular slots 210 begin to close so that the segments 211 move towards each other and eventually touch at the outer periphery of the bendable and flexible section 202. This facilities the enhanced steerability of the steerable cannula 200. It is noted that the slots are preferably provided on the inside 218 of the curve of the cannula so that as the probe needle 28 is inserted through the steerable cannula 200, that probe needle will be forced towards the outside radius 220 of the steerable cannula 200 away from the inside radius 218 so that the probe needle 28 will not become engaged with or project through the semi-circular slots 210.

Figure 14B:
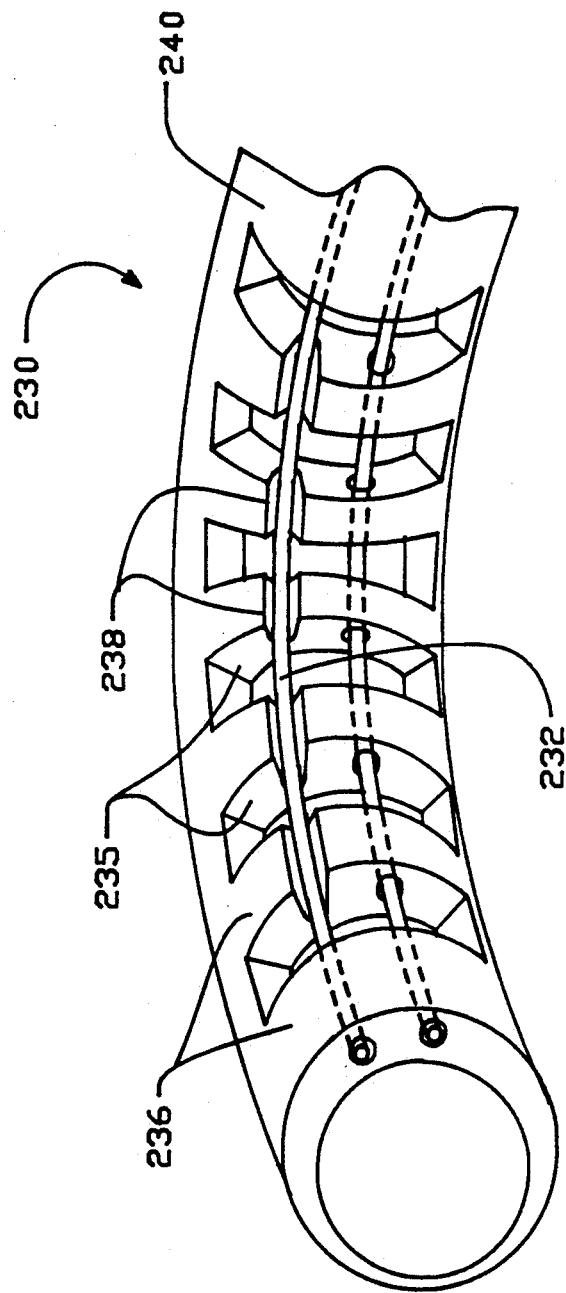

FIGS. 14A and 14B depicts yet another embodiment 230 of the steerable cannula. Steerable cannula 230 is similar to steerable cannula 200 (FIG. 9) in design. However in the embodiment of FIG. 14A, 14B, a side bore 234 where it is located discretely through the segment 236, is provided with apertures 238 which are opened to the surface 240 of the steerable cannula 230. Thus, the embodiments of FIGS. 14a and 14b incorporate the advantages as taught in the embodiment of the steerable cannula in FIGS. 7 and 8 and also as taught in the embodiment of FIGS. 9 through 13 in that the steerability is enhanced by the plurality of semi-circular slots 235 and by the ability of the tether 232 to extend at defined locations away from the steerable cannula 230.

Figure 15:
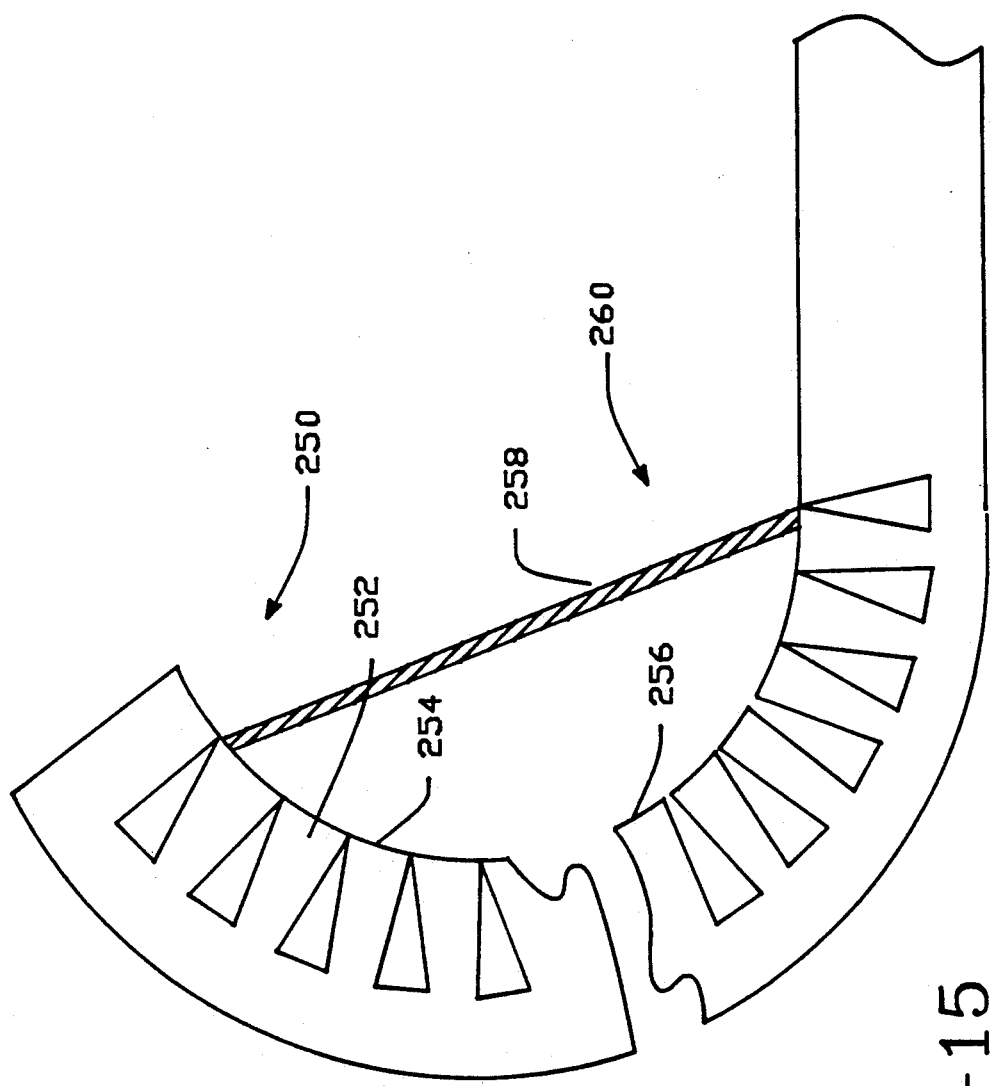
FIG. 15 depicts yet an alternative embodiment of the steerable cannula.

Yet another embodiment of the steerable cannula is identified by the number 250 in FIG. 15. This embodiment is substantially similar to the embodiment as shown in FIGS. 14a and 14b with the exception that all of the segments 252 have apertures 254 which are opened to the surface 256 of the steerable cannula 250 such that the tether 258 can project away from the steerable cannula 250 for the entire length of the flexible section 260 which is comprised of the segments 252.

In the embodiment of FIGS. 1 through 15, due to the spaced apart segments allowing for greater bendability, alternatively the entire cannula body can be extruded of a thermoplastic elastomer without the need for a separate cannula body such as body 98 in FIG. 4 which would, for example, be made of a stainless steel. In such an embodiment, the portion of the thermoplastic body without the spaced apart segments would be the rigid section and the portion of the thermoplastic body with the spaced apart segments would be the bendable sections.

Figure 16:
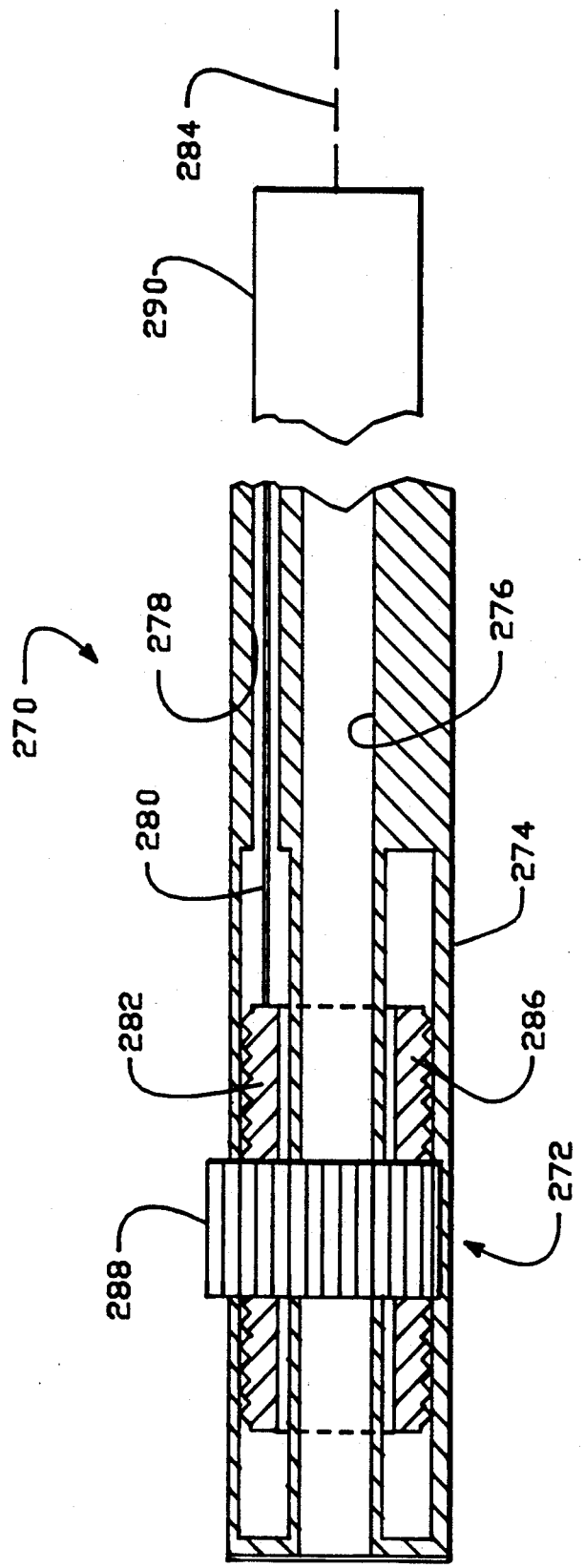
FIG. 16 depicts a side cross-sectional view of a tether retraction mechanism of an embodiment of the steerable cannula of the invention.

Still another embodiment of the steerable cannula 270 of the invention is shown in FIG. 16. This embodiment focuses on the handle 272 of the steerable cannula 270. This handle 272 can be used with the flexible and bendable sections of all the other steerable cannulas described hereinabove. The steerable cannula 270 includes an outer substantially tubular and rigid body 274 which can, for example in a preferred embodiment, be comprised of stainless steel. This body defines central bore or lumen 276 which can receive the probe needle 28 as depicted in FIG. 2. The tubular body 274 additionally defines a side bore or lumen 278, in which is deposed a tether 280. Tether 280 is used to bend the cannula as taught hereinabove.

The tether 280 is attached to a threaded shaft 282 which is mounted for movement along the longitudinal axis 284 of the steerable cannula 270. The threaded shaft 282 includes a central bore 286 through which the central bore 278 which receives the probe needle 28 is positioned. A thumb wheel 288 is provided about the threaded shaft 282 and mounted for rotation in the handle 272. The thumb wheel 288 includes threaded which mate to the threaded shaft 282. As the thumb wheel 288 is turned or rotated about the longitudinal axis 284, the threaded shaft 282 is caused to move along the longitudinal axis relative to the thumb wheel 288 which in turn causes the tether to be moved along the longitudinal axis so as to adjust the position of the end 290 of the steerable cannula 270.

Industrial Applicability

As can be seen from the aforementioned embodiments, the present invention provides for a percutaneous discectomy system having a bandable discectomy probe and a steerable cannula in order to allow for a wide range of positioning capabilities for the removal of herniated disc tissue and for that matter, any tissue located anywhere in the body. For example, such a probe could be used to remove damaged or cancerous brain tissues and the like. With the present embodiment, the steerable cannula can be inserted through the bodily tissues to a desired surgical location. The exact position of the cannula can be adjusted as described above by using the tethers. Thereafter, the bendable probe can be inserted through the cannula. Tissue can be removed along the line extending from the end of the cannula. Thereafter, the steerable cannula can be repositioned through the use of the tethers or other means without having to withdraw the cannula from the body and thus with minimum additional trauma to the adjacent tissues. Once the cannula has been repositioned, the bendable probe can be extended out of the end of steerable cannula along a new line and remove tissue. This process can be repeated an many times as is required to remove the appropriate amount of tissue without having to remove the steerable cannula from the body and reposition it through a different entry point or through the same entry point along a different line.

It is to be understood that other embodiments of the present invention can be obtained from a review of the claims and the appended figures.

It is further to be understood that other embodiments of the invention can be fashioned and come without the spirit and scope of the appended claims.

We claim:

1. A surgical instrument comprising:
   a probe body;
   an elongate probe needle with a longitudinal axis extending from said probe body and an end located distally from said probe body, and having a tissue removing means for removing tissue and an elongate outer tubular body, said elongate probe needle further having:
   a first repeatably bendable section in said elongate outer tubular body in order to allow for selective positioning of said cutting means relative to said longitudinal axis,
   an elongate inner tubular body within said elongate outer tubular body, said elongate inner tubular body including a second repeatedly bendable section, said second repeatably bendable section for allowing selective positioning of said tissue removing means relative to said longitudinal axis,
   irrigation means for delivering irrigation fluid,
   aspiration means for removing irrigation fluid and tissue, and
   wherein said first and second repeatably bendable section allow said tissue removing means to be repeatably positioned to a location away from said longitudinal axis.

2. The surgical instrument of claim 1 wherein:
said irrigation means includes a first passage; and
said aspiration means includes a second passage adjacent to the first passage.

3. The surgical instrument of claim 1 wherein:
said first and second bendable sections are comprised of an elastic material.

4. The surgical instrument of claim 1 wherein said tissue removing means includes a reciprocating cutting blade.

5. The surgical instrument of claim 1 wherein said tissue removing means includes means for delivering light capable of removing tissue.

6. The surgical instrument of claim 5 wherein said light delivering means is a laser.

7. The surgical instrument of claim 1 wherein:
said elongated outer tubular body includes a substantially rigid section being comprised of a non-elastic material.

8. The surgical instrument of claim 1, wherein:
said irrigation means is defined by an annular passage between said elongate outer tubular body and said elongate inner tubular body; and
said aspiration means is defined by a passage in said elongate inner tubular body.

9. The surgical instrument of claim 1 including:
a steerable cannula with an internal passage for receiving and steerably positioning said probe needle.

10. The surgical instrument of claim 1 further including:
means adjacent to the tissue cutting means for providing a source of illumination of a surgical site; and
means adjacent to the tissue cutting means for communicating an image of the surgical site.

11. The surgical instrument of claim 9 wherein the steerable cannula includes a plurality of tethers for steering the cannula.

12. The surgical instrument of claim 9 including:
a bendable portion and a substantially rigid portion in said steerable cannula;
a tether connected between said bendable portion and said rigid portion; and
means for moving the tether and the bendable portion relative to the rigid portion in order to position said tissue removing means relative to said longitudinal axis with the probe needle received in the internal passage of the cannula.

13. The surgical instrument of claim 12 including:
a plurality of spaced apart segments provided in the bendable portion of said cannula.

14. The surgical instrument of claim 13 including:
said plurality of spaced apart segments provided substantially across a longitudinal axis of the steerable cannula.

15. The surgical instrument of claim 13 including:
a bore means defined in said bendable portion for receiving said tether, said bore means provided through the spaced apart segments.

16. The surgical instrument of claim 12 including:
a bore means for receiving the tether, which bore means is located in the bendable portion;
said steerable cannula defining an outer surface; and
a plurality of elongate apertures which communicate the bore means with the outer surface of the steerable cannula so that as the cannula is steered the tether projects out of the elongated apertures and becomes spaced from the outer surface of the cannula.

17. The surgical instrument of claim 16 including:
a plurality of spaced apart segments provided in the bendable portion, said bore means provided through said segments.

18. The surgical instrument of claim 12 including:
said steerable cannula having a longitudinal axis; and
said tether moving means including means for rotations about the longitudinal axis of the steerable cannula for causing the tether to move.

19. A surgical instrument comprising:
a probe body;
an elongate probe needle with a longitudinal axis extending from said probe body;
said probe needle including means adapted for removing tissue;
said probe needle including a repeatably bendable section which is located adjacent to said tissue removing means in order to allow for selective positioning of the tissue removing means in a wide range of positions relative to the longitudinal axis; and
said probe needle including a substantially rigid section which is located between said bendable section and said probe body;
said elongate probe needle including an outer elongate and hollow cylinder and an inner elongate and hollow cylinder;
said outer cylinder including an outer elastic section which comprises in part, said bendable section; and
said inner cylinder including an inner elastic section which comprises in part, said bendable section.

20. The surgical instrument of claim 19 including:
irrigation means defining an annular passage between said outer and inner cylinder; and
aspiration means defining a passage in said inner cylinder.

21. A surgical instrument comprising:
a probe needle having a length and a means for removing tissue;
said probe needle having an elongate outer tubular portion, said elongate outer tubular portion having a first repeatably bendable section;
said probe needle having an elongate inner tubular portion within said elongate outer tubular portion, said elongate inner tubular portion including a second repeatably bendable section;
said first and second repeatably bendable sections allowing the probe needle to provide a variable bend along the length in order to position the removing means.

22. The probe needle of claim 21, wherein said first and second repeatably bendable sections are capable of being formed into a 90° angle or less.

23. The probe needle of claim 21, wherein said first and second repeatably bendable sections are comprised of elastic material.

24. The probe needle of claim 21, wherein said first and second repeatably bendable sections are located adjacent each other.

25. A surgical instrument comprising:
a probe body;
an elongate probe needle with a longitudinal axis extending from said probe body;
said probe needle including means adapted for removing tissue;
said probe needle including irrigation means for delivering irrigation fluid;

said probe needle including aspiration means for removing irrigation fluid and tissue;

said probe needle including a repeatably bendable section which is located between said probe body and said means for removing tissue in order to allow for selective positioning of the tissue removing means relative to the longitudinal axis and through which bendable section passes the irrigation means and the aspiration means;

wherein said repeatably bendable section allows said tissue removing means to be repeatably positioned to a location away from the longitudinal axis;

said elongate probe needle includes an outer elongate and hollow cylinder and inner elongate and hollow cylinder;

said outer cylinder includes an outer elastic section which comprises in part, said bendable section; and said inner cylinder includes an inner elastic section which comprises in part, said bendable section.

26. The surgical instrument of claim 25 including:

said irrigation means defining an annular passage between said outer and inner cylinder; and said aspiration means defining a passable in said inner cylinder.

27. The surgical instrument of claim 25 further including:

means adjacent to the tissue removing means for providing a source of illumination; and means adjacent to the tissue removing means for communicating an image of the surgical site.

* * * * *